United States Patent
List

(10) Patent No.: US 8,262,684 B2
(45) Date of Patent: Sep. 11, 2012

(54) LANCET SYSTEM WITH A STERILE PROTECTOR

(75) Inventor: Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 561 days.

(21) Appl. No.: 11/939,673

(22) Filed: Nov. 14, 2007

(65) Prior Publication Data

US 2008/0125800 A1    May 29, 2008

Related U.S. Application Data

(63) Continuation of application No. PCT/EP2006/062385, filed on May 17, 2006.

(30) Foreign Application Priority Data

May 20, 2005 (EP) .................................. 05011037

(51) Int. Cl.
*A61B 17/32* (2006.01)
(52) U.S. Cl. ........................................ 606/181; 606/183
(58) Field of Classification Search ................ 606/181, 606/182, 183; 604/59–64, 136, 139; 600/573, 600/578, 583, 584
See application file for complete search history.

(56) References Cited

U.S. PATENT DOCUMENTS

| 2,754,822 | A | * | 7/1956 | Emelock | 604/59 |
| 3,667,465 | A | * | 6/1972 | Voss | 604/59 |
| 3,934,584 | A | * | 1/1976 | Corio | 604/59 |
| 5,304,192 | A |  | 4/1994 | Crouse | |
| 5,554,166 | A |  | 9/1996 | Lange et al. | |
| 6,616,616 | B2 | * | 9/2003 | Fritz et al. | 600/583 |
| 7,144,386 | B2 | * | 12/2006 | Korkor et al. | 604/164.03 |
| 2003/0050573 | A1 |  | 3/2003 | Kuhr et al. | |
| 2003/0130597 | A1 | * | 7/2003 | Marshall | 600/583 |
| 2003/0153939 | A1 |  | 8/2003 | Fritz et al. | |
| 2003/0199893 | A1 | * | 10/2003 | Boecker et al. | 606/181 |
| 2004/0034318 | A1 |  | 2/2004 | Fritz et al. | |
| 2004/0064082 | A1 | * | 4/2004 | LeMay et al. | 604/11 |
| 2004/0260325 | A1 |  | 12/2004 | Kuhr et al. | |
| 2005/0021066 | A1 | * | 1/2005 | Kuhr et al. | 606/181 |
| 2005/0027211 | A1 | * | 2/2005 | Kuhr et al. | 600/583 |

FOREIGN PATENT DOCUMENTS

| GB | 2421439 | A | * | 6/2006 |
| JP | 37432/1974 | | | 10/1974 |
| WO | WO 01/66010 | | | 9/2001 |
| WO | WO 02/36010 | | | 5/2002 |

* cited by examiner

*Primary Examiner* — Ryan Severson
*Assistant Examiner* — David Eastwood
(74) *Attorney, Agent, or Firm* — Bose McKinney & Evans LLP

(57) ABSTRACT

The present invention provides a lancet system having a lancet tip protected by a sterile protector. The sterile protector includes a weakened portion near the tip end of the protector, which, during a puncturing operation, separates or tears in order to release the lancet tip. Other embodiments of the present invention include a pricking aid and/or lancet system provided as a magazine for holding a plurality of lancets. Each lancet of the plurality has a sterile protector as described above.

40 Claims, 3 Drawing Sheets

LANCET SYSTEM WITH A STERILE PROTECTOR

RELATED APPLICATIONS

This application is a continuation application of International Application PCT/EP2006/062385, filed May 17, 2006, which claims priority to EP 05 011 037, filed May 20, 2005, which are hereby incorporated by reference in their entirety.

BACKGROUND

The present invention generally relates to a lancet system, and more particularly relates to a lancet system comprising at least one lancet having a lancet tip protected by a sterile protector.

The removal of body fluids such as blood is performed with the aim of subsequent analysis to diagnose illnesses or monitor the state of a patient's metabolism. Diabetics, in particular, remove samples of blood to determine the concentration of blood sugar. In order to remove only small amounts of blood, sharp, sterile lancets are quickly pierced into a patient's fingertip or other body part, for example, by hospital staff or by the patient himself. Lancet systems and other similar devices (for example, blood taking equipment, blood lancet devices, or pricking aids) which extract blood with minimal pain and in a reproducible manner are provided especially in the area of "home-monitoring," in which lay people carry out simple analyses of their blood.

Lancet tips used for blood extraction are typically sterilized in advance and are stored in a sterile state via a sterile protector (for example, in the form of a cap or pocket) before the lancet is used for a puncturing operation to prevent the tip from being contaminated by the surroundings. Furthermore, measures are frequently taken to ensure that, after a puncturing operation has taken place, the lancet tip is shielded or protected again (for example, by the same cap or pocket) to prevent injury and infections from blood that remains adhered to the lancet tip.

In the case of individual lancets, a sterile protector can be produced, for example, by encapsulating the lancet tip with plastic by injection molding both the lancet body and sterile protector during the same process. Before the lancet is used, the user manually removes the sterile protector upon inserting the lancet body into a pricking aid. In the case of lancets being encased in a magazine, similar sterile protectors are customary in which the lancet is pulled out of the sterile protector, whereby the sterile protector is moved out of the puncture path by a spring force. Relatively complicated mechanisms, such as springs, are integrated into the equipment to carry out this function.

Document WO 01/66010 discloses a lancet system that circumvents the complicated nature of this mechanism by piercing the sterile protector. In particular, document WO 01/66010 relates to a lancet comprising a lancet needle with a tip and a lancet body which completely surrounds the lancet needle at least in the region of the tip. In the region around the tip, the lancet body is composed of an elastic material in which the tip of the lancet needle is embedded. Furthermore, a lancet is disclosed having a lancet needle with a tip and a hollow body which surrounds at least the tip of the lancet needle. The lancet needle is movable in the region of its tip inside the hollow body or housing, and the hollow body or housing is at least partially composed of an elastic material which can be punctured by the tip of the lancet needle during the puncturing operation. Further, and if appropriate, the hollow body or housing closes again after the tip of the lancet needle completes a puncturing operation and is retracted into the hollow body or housing. A disadvantage of this lancet is that the elastic enclosure causes friction along the entire puncture path. Therefore, the drive units or actuators used to move the lancet have to be appropriately dimensioned to carry out the operation. However, enclosing the used lancet tip in this manner is unnecessary in many aspects in which the lancet is held in a magazine or is individually present, because the lancet tip is retracted, for example, into a rigid hollow body or housing and therefore the risk of contaminating the surroundings or risk of injury from the tip is reduced.

U.S. Pat. No. 5,304,192 relates to a lancet device having a lancet needle and a tip which is enclosed by a removable cap. The cap ensures that the lancet tip remains sterile before use. The cap is connected to another component of the lancet device via a breakable connection and is manually twisted off from said component.

U.S. Pat. No. 5,554,166 relates to a blood lancet device with a lancet needle which, in the unused state, is provided with a sterile protective cap. For removal, the sterile protective cap is twisted in such a manner that it breaks off at predetermined tear points.

Manually removing protective caps to release the lancet tip for a puncturing operation is a step to be avoided in a method for removing body fluids, since it complicates the handling of such lancets.

SUMMARY OF THE INVENTION

Embodiments incorporating the present invention address the above-described disadvantages of the prior art and provide lancet systems or magazines in which at least a lancet tip is kept sterile in an unused state before it is used for the first time, and after it has been used, the lancet tip is stored in such a manner that the risk of contaminating the surroundings and unintentional injury sustained by the user is reduced. Furthermore, these embodiments reduce the friction between the lancet needle, and in particular the lancet tip, against a sterile protector during both the puncture and the retraction of the lancet tip. Therefore, drive units of a pricking aid can be made less powerful, the degree of wear on all of the movable parts of the pricking aid can be reduced, and the service life of the pricking aid can be improved.

An exemplary embodiment provides a lancet system which contains at least one lancet with a lancet tip. The lancet tip is surrounded by a sterile protector, the latter of which includes a weakened portion(s) of material that is brittle and has a tendency to undergo brittle fracture or tearing, such that the sterile protector separates along the weakened portion(s) into subregions. The weakened portion(s) may also be made of perforated material that tears along perforated sections. In one embodiment, the sterile protector includes predetermined tear sections which are made of brittle material, and during a puncturing operation, the tear sections separate or tear in order to release the lancet tip. In this embodiment, the tip also moves or slides relative to the sterile protector. The tear sections may comprise a groove or indentation in the sterile protector.

The lancet system has at least one lancet with a lancet tip. In another embodiment, the lancet system has multiple lancets. The lancet system can be a magazine for holding lancets that is inserted into a lancing aid or instrument.

When the lancet system is used correctly, the lancet tip pierces body tissue in order to cause body fluid, in particular blood or interstitial fluid, to flow out of the tissue. In one embodiment, the lancet tip may have, for example, a rotationally symmetrical design (for example, a conical or cylindrical"

shape). One or more polished sections may also be provided on the lancet tip. In a different embodiment, the edges of the tip can be inclined towards the longitudinal axis of the lancet tip and taper inwards toward the tip (for example, a blade-like cutting edge). Accordingly, this particular lancet tip has a sharp cutting edge and performs the puncturing operation in an advantageously less painful manner than is the case with rotationally symmetrical lancet tips.

The sterile protector of the lancet system shields an unused lancet tip in a germproof manner, and therefore germs cannot contaminate the lancet tip until immediately before the lancet system is used. After being sterilized, the lancet tip remains sterile in the sterile protector over an extended period of time. The sterile protector can be, for example, a hollow body or housing surrounding the lancet tip. The lancet tip may also be embedded in the sterile protector, with it being possible for the sterile protector to be produced, for example, by encapsulating the lancet tip by injection molding. Further, the tip may be embedded or encapsulated by a sterile protector and both the tip and sterile protector are movably mounted or disposed in a hollow body or housing.

The sterile protector comprises a weakened portion that separates or tears without having any lasting change in shape if a force is applied to it prior to separating or tearing. In other words, the weakened portion of the sterile protector that is brittle or perforated has a tendency to separate or tear before it changes shape through deformation. In an advantageous embodiment, the yield point of the weakened portion is approximately identical to its separating or tearing point. For example, if a lancet tip is made of steel with a yield point of approximately 500 N/mm$^2$, the weakened portion of the sterile protector should have a yield point which is below 50 N/mm$^2$. This weakened portion advantageously has a high degree of brittleness and a low strength such that little energy is required to at least partially separate or tear the sterile protector along the weakened portion of the sterile protector. In particular, the material of the weakened portion should be soft in relation to the material of the lancet tip and/or needle such that the latter is not damaged as the weakened portion separates or tears. For a lancet tip made of steel with a Vickers hardness of approximately 250, for example, the Vickers hardness of the weakened portion should advantageously be below 25.

In the case of the lancet system, the weakened portion may comprise brittle material. The weakened portion has predetermined tear sections at which the material separates or tears when a force is applied to it and thus releases the lancet tip to carry out a puncture operation. Therefore, the tip is able to move or slide in a puncture direction relative to the sterile protector. This design of the sterile protector of the lancet system has the advantage that it can separate or tear without a large force being applied to it, and once the sterile protector separates or tears, the lancet tip can move or slide substantially without friction relative to the sterile protector (for example, out of a hollow body, housing, or pricking aid). A pricking aid or lancing device, which is used for the puncturing operation and into which the lancet system is inserted, therefore does not require a powerful drive unit and is subjected to less wear.

In one embodiment, the sterile protector is separated or torn by the lancet tip or the entire lancet needle. In this embodiment, the lancet needle, and in particular the lancet tip, applies a force to the weakened portion of the sterile protector. Therefore, the sterile protector advantageously does not have to be opened and removed manually in a complicated manner, but rather is automatically separated by the lancet needle as the puncturing operation is carried out.

In a different embodiment, the weakened portion of the sterile protector comprises a thermoplastic containing a filler, a metal soap containing a filler, or a wax containing a filler. Thermoplastics can be processed in a softened state by pressing, extruding, injection molding, or any other shaping method to form shaped parts. The material properties of thermoplastics can be varied, inter alia, by the addition of fillers. For embodiments incorporating the present invention, the brittleness of the thermoplastic, wax, or metal soap is yielded by adding a filler, which is what produces the weakened portion of the sterile protector that has more of a tendency of undergoing brittle fracture than deformation. The melting point of the weakened portion should generally be greater than 70° C. so that the sterile protector can be stored without encountering problems.

The filler can be advantageously selected from the group consisting of talc, graphite, and molybdenum disulfide. The wax can be selected from the group consisting of paraffins, stearins, synthetic waxes (for example, polyethylene waxes), and natural waxes (for example, beeswax). Suitable metal soaps are salts from the metals Al, Ba, Ca, Cd, Co, Cr, Cu, Fe, Mg, Mn, Ni, Pb, Sn, Sr, and Zn along with higher fatty, resinic, or naphthenic acids (such as stearates, palmitates, oleates, linoleates, laurates, etc.). Suitable metal soaps are generally selected from the group consisting of aluminum stearate, aluminum palmitate, calcium stearate, calcium palmitate, magnesium stearate, magnesium palmitate, zinc stearate, or zinc palmitate, and particularly aluminum stearate (such as aluminum monostearate, distearate, or tristearate, depending on the type), calcium stearate, or magnesium stearate. The thermoplastic is typically selected from the group consisting of polyethylene and polypropylene. In particular, soft thermoplastics (for example, polyethylene) which are filled with a high proportion of talc are suitable for the weakened portion of the sterile protector. Talc is a soft material which does not damage the polished section of the needle tip when the weakened portion separates. The talc particles are readily suitable to reduce the inner strength of the thermoplastic, wax, or metal soap such that a viscoelastic behavior is displaced in the brittle direction without the hardness of the thermoplastic, wax, or metal soap increasing. The amount of filler in the thermoplastic is advantageously more than 20% of the volume, and is particularly advantageous when between 20 and 50% of the volume.

In a different embodiment, the predetermined tear sections are arranged substantially parallel to the lancet tip and extend at least over a portion of the length of the sterile protector. The sterile protector may be, for example, a cylindrical cap which rests on the lancet tip. In this embodiment, the predetermined tear sections extend in the puncture direction along the circumferential surface of the cylindrical cap. They may run along the entire length of the circumferential surface or only a portion of the length of the circumferential surface (in the region of the lancet tip). In the embodiment where the tear sections extend along only a portion of the length of the sterile protector, a second or adjoining portion adjoins the weakened portion. In this particular embodiment, when the weakened portion at least partially separates at the tear sections, the second or adjoining portion does not separate or tear. Instead, the weakened portion remains connected to the sterile protector via the second or adjoining portion, which remains surrounding the lancet after the weakened portion begins to separate or tear.

In another embodiment, the predetermined tear sections divide the weakened portion of the sterile protector into subregions. These subregions protrude away from the lancet tip after the sterile protector is separated at the tear sections.

After the separation occurs, the protruding subregions adhere or remain attached to the lancet tip or sterile protector such that they are not loosely contained in an uncontrolled manner in the lancet system. The sterile protector may be manufactured from the same material as the weakened portion, for example, in the region where the tear sections divide the sterile protector into subregions. Additionally, the sterile protector may be manufactured from different materials such that there is a point along the length of the sterile protector at which the weakened portion adjoins a non-brittle or non-perforated portion, and the material at this adjoining point is made from a plastically deformable material. This plastically deformable material forms the second or adjoining portion as described above. In this particular sterile protector, the weakened portion separates or tears at the predetermined tear sections and are held protruding away from the lancet tip by the adjoining portion. However, the sterile protector may also be manufactured entirely from the same material as the weakened portion. In this particular sterile protector, although the subregions of the weakened portion are separated from one another at the predetermined tear sections during the puncturing operation, they remain connected to a part of the sterile protector that does not have any predetermined tear sections. Accordingly, the subregions protrude at an angle from the lancet tip. These subregions, which protrude from the lancet tip after separating or tearing from the sterile protector, have the advantage that, after the lancet tip is released, the subregions are not loosely contained, for example, within a hollow body, housing, or pricking aid, nor do they interfere with the movement of the lancet tip.

In a different embodiment, the lancet system contains a lancet needle which includes a tip and needle body, wherein the needle body is at least partially surrounded by a lancet body. In this embodiment, the lancet body may be fixedly connected to the needle body or the needle body may be movable relative to the lancet body (in order to carry out the puncturing operation). The lancet body may partially or completely surround the needle body. The lancet needle can be manufactured from a material which is sufficiently hard in order to withstand, without deformation, a mechanical stress applied to it during a puncturing operation, and in particular, when the weakened portion of the sterile protector separates, and/or during the processing steps or when subjected to any other stresses. Furthermore, the material has to be provided such that no particles break off or become detached from the lancet needle during the puncturing operation. Finally, the lancet needle also has to be able to be processed in such a manner that the lancet tip can be polished to a sufficiently sharp point and the edges of the lancet tip can, if necessary, be polished to a sufficient degree of sharpness. Suitable materials for the lancet needle include various metals, and in particular specialty steels. However, needles made of ceramic or plastic are also possible.

In another exemplary embodiment, the lancet system comprises a hollow body or housing which surrounds at least the lancet tip and the lancet tip is movable in the hollow body or housing. The hollow body or housing provides protection to a user against unintentional injury from the lancet tip, and in particular, after a puncturing operation has taken place and the lancet tip is retracted into the hollow body or housing. The lancet tip is movable relative to the hollow body or housing such that it can be moved out of the hollow body or housing to carry out a puncturing operation. The hollow body or housing advantageously has an outlet opening through which the lancet tip can emerge during a puncturing operation and retract into the hollow body or housing through the outlet opening after the puncturing operation.

In one embodiment, the hollow body or housing has a tubular design with both of its ends having openings which may be open or closed. For example, both ends may be closed by films made of an elastic or plastic material which can be punctured and thereby opened during the puncturing operation. One of the two openings can serve as the outlet opening for the lancet tip to pass through during the puncturing operation. An actuating means or actuator, such as a ram or hook, can pass through the other opening and move the lancet tip during a puncturing operation.

The lancet body may be movable relative to or fixedly connected to the hollow body or housing. In the former instance, the lancet needle is fixedly connected to the lancet body and, in the latter instance, it is movable inside the hollow body or housing relative to the lancet body. The lancet body can serve as a guide element for the lancet needle.

In an advantageous embodiment, a hollow body or housing completely surrounds the lancet body and the lancet tip and the lancet body and the lancet tip are displaceable together in the hollow body or housing. In this embodiment, the lancet body and the lancet tip are advantageously displaceable in the longitudinal direction with respect to the lancet tip.

For the separate or joint movement of the lancet tip and lancet body, corresponding structural elements or mechanisms (for example, actuating means, drive unit, or securing elements) can be provided in a pricking aid in which the lancet system is used.

In a different embodiment, the sterile protector comprises a first end section and a second end section. The second end section includes a weakened portion(s) or predetermined tear sections, wherein the sterile protector can be displaced on the lancet needle away from the lancet tip after being separated at the weakened portion(s) or predetermined tear sections of the second end section. In this embodiment, the second end section of the sterile protector separates or tears at the weakened portion(s) near the lancet tip and releases the lancet tip for a puncturing operation. However, the sterile protector, and in particular the first portion, remains intact and surrounds the lancet needle. The second end section, including the weakened portion, also remains attached or connected to the sterile protector, and in particular the first end section. Therefore, the sterile protector is displaced, e.g., by sliding, on the lancet needle away from the lancet tip. This design of the lancet system has the advantage that, during the puncturing operation, the sterile protector, and in particular the second end section, cannot become loosely separated, for example, in the hollow body, housing, or pricking aid, nor interfere with the puncturing operation.

For the lancet needle or lancet tip to separate or tear the sterile protector at the weakened portion, it has to exert a force on the weakened portion. In one embodiment, the sterile protector can be fixed to a hollow body or housing and the lancet needle or lancet tip can be pushed through the sterile protector. However, in a second embodiment, the lancet tip is movable together with the sterile protector in a hollow body or housing such that the sterile protector collides against a surface, such as an inner surface of the hollow body or housing in order to break the sterile protector at its predetermined tear sections and allows the lancet tip to be driven through the sterile protector. In this case, the sterile protector (designed, for example, as a cylindrical cap) is moved together with the lancet tip until it strikes against the surface and breaks thereon and/or is slowed down by the inner surface such that the lancet tip is driven through the sterile protector. The lancet tip can then emerge through an outlet opening in the hollow body, housing, or pricking aid in order to carry out the puncturing operation. Accordingly, the lancet tip moves or slides relative to the sterile protector.

Furthermore, in another embodiment, a lancet system is designed as a magazine that holds a plurality of lancets. Each of the plurality of lancets has a lancet tip and is contained in an individual chamber of the lancet system. The plurality of lancets are independent from each other and each lancet tip is movable within its respective chamber. In this embodiment, the lancet tip is surrounded in the chamber by a sterile protector, which is at least partially composed of a brittle material that tends to separate rather easily. The sterile protector has predetetiinined tear sections and, during a puncturing operation, is separable at the predetermined tear sections in order to release the lancet tip to complete a puncturing operation.

The lancet system, when provided as a magazine, stores the unused and used lancets. The chambers of the magazine are functionally similar to the hollow body or housing of the above-described lancet system. The chambers are advantageously arranged in a geometrical fashion in the magazine, with it being possible for adjacent chambers to share common walls. The magazine may be constructed, for example, in the form of a stack, disk, or drum.

The lancet tips are stored in their respective sterile protectors before they are used to maintain sterility. During a puncturing operation, the weakened portion of the sterile protector is separated at the predetermined tear sections with the aid of the lancet needle, in particular with the aid of the lancet tip, such that the lancet tip is released for the puncturing operation. Accordingly, the lancet tip emerges out of its chamber through an outlet opening. After the puncturing operation, the lancet tip is retracted into its chamber through the outlet opening to prevent an unintentional injury from the lancet tip and/or contaminating the surroundings.

In a different embodiment, a pricking aid is provided and it comprises at least one lancet system and an actuating means or actuator. The actuating means or actuator can act on the lancet system to move the lancet tip, for example, in the hollow body or housing, the pricking aid, or the chamber, such that the lancet tip can break the sterile protector at its predetermined tear sections and emerge from the hollow body or housing, the pricking aid, or the chamber to perform a puncturing operation. The lancet systems are inserted individually and manually into the pricking aid by the user. For example, multiple lancets, which are being held in a lancet system in the form of a magazine, can be inserted into the pricking aid. An actuating means or actuator (for example, a ram or hook) acts on an individual lancet so as to move the lancet tip to separate or tear the weakened portion of the sterile protector at its predetermined tear sections and carry out the puncturing operation. Furthermore, the actuating means or actuator can retract the lancet tip into its hollow body or housing, into the pricking aid, or into its chamber after a puncturing operation. However, a further element (for example, a spring) may also be provided in the pricking aid for this purpose.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1C:
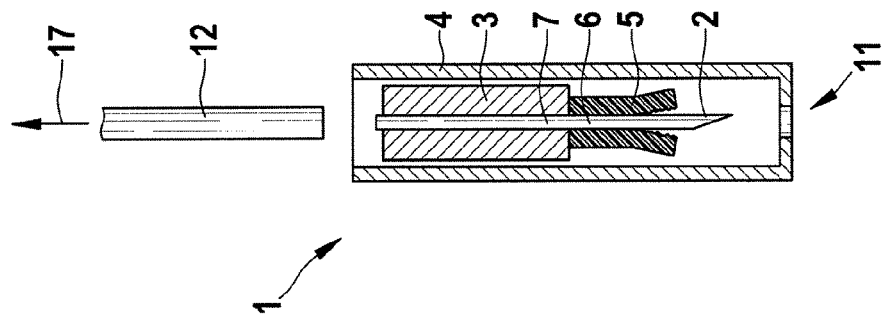
FIGS. 1a-1c are schematic views shown in partial cross-section of a lancet system having a tip being moved in a puncture and retracting direction.
Figure 1B:
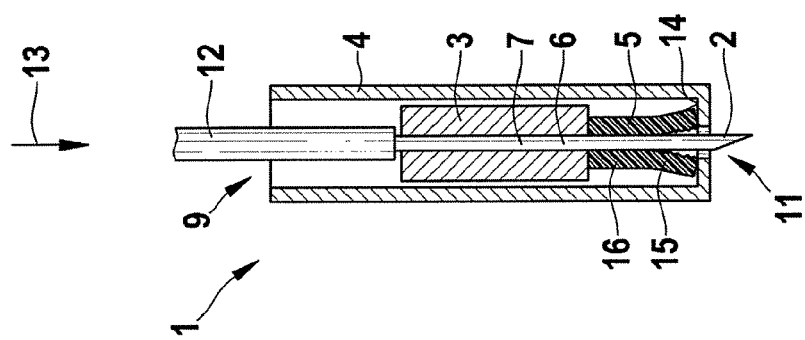
Figure 1A:
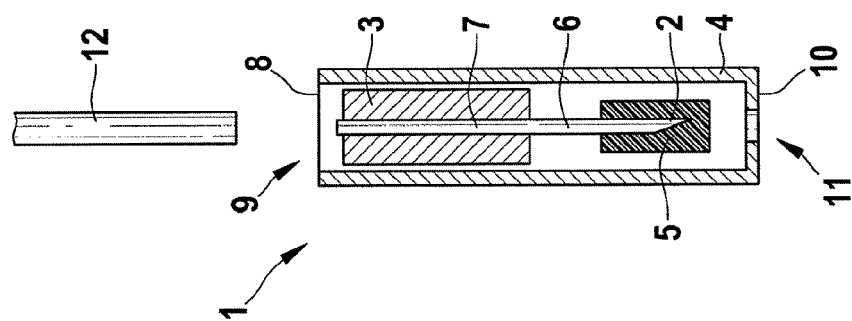

The lancet system 1 of FIG. 1 has a lancet tip 2, a lancet body 3, and a hollow body or housing 4. In FIG. 1a, the lancet system 1 is being shown prior to use. The lancet tip 2 is encapsulated in the hollow body or housing 4 by a sterile protector 5, which has a weakened portion of material that can undergo brittle fracture or separation. The sterile protector 5 is a cylindrical cap which rests on the lancet tip 2 and has predetermined tear sections 18 (see FIG. 2).

The lancet system 1 also contains a lancet needle 6 which comprises the lancet tip 2 and a needle body 7, wherein the needle body 7 is partially surrounded by the lancet body 3. The lancet body 3 serves as a guide element for the lancet needle 6 and is movably disposed inside the hollow body or housing 4. The hollow body or housing 4 has a tubular design with a first opening 9 formed at a first end 8 facing the opposite direction from which the lancet tip 2 points, and a second opening 11 formed at a second end 10 facing in the same direction as the lancet tip 2. The hollow body or housing 4 completely surrounds the lancet body 3, the lancet needle 6, and the sterile protector 5, wherein these three elements are movable in the longitudinal direction together inside the hollow body or housing 4. An actuating means or actuator 12 is provided, for example, in the pricking aid to actuate the lancet system 1 to carry out a puncturing operation.

FIG. 1b shows a puncturing operation being performed by the lancet system 1. In this embodiment, the actuating means or actuator 12 is moved through the first opening 9 into the hollow body or housing 4. The actuating means or actuator 12 exerts a force in the puncture direction 13 on the lancet body 3, lancet needle 6, and sterile protector 5. As a result, these elements of the lancet system 1 move towards the second opening 11 of the hollow body or housing 4 until the sterile protector 5 collides against an inner surface 14 of the hollow body or housing 4, wherein the inner surface 14 surrounds the second opening 11, and the lancet tip 2 is driven through the sterile protector 5. Accordingly, the weakened portion of the sterile protector 5 breaks at the predetermined tear sections and releases the lancet tip 2 to move or slide relative to the sterile protector 5. The lancet tip 2 emerges out of the hollow body or housing 4 through the second opening 11, and produces a prick or puncture, for example, in a user's finger. The sterile protector 5 is displaced away from the lancet tip 2 in a region 15 where the predetermined tear sections are present. Additionally, the sterile protector 5 remains intact with the lancet needle 6 in a second region 16 where the predetermined tear sections are not present and thus the sterile protector 5 still surrounds the lancet needle 6. Therefore, there are no loose fragments of the sterile protector 5 in the hollow body or housing 4.

FIG. 1c shows the lancet tip 2 being retracted through the outlet opening 11 and into the hollow body or housing 4 after the puncturing operation. The retraction can be brought about, for example, by the actuating means or actuator 12, which sticks to the lancet body 3 (for example, is interlocked therewith) and pulls it in the retracting direction 17. Due to the hollow body or housing 4, which surrounds the lancet tip 2 in a protective manner following retraction, a risk of injury due to the used lancet tip 2 is avoided, as is contaminating the surroundings due to body fluid adhering to the lancet tip 2.

Figure 2:
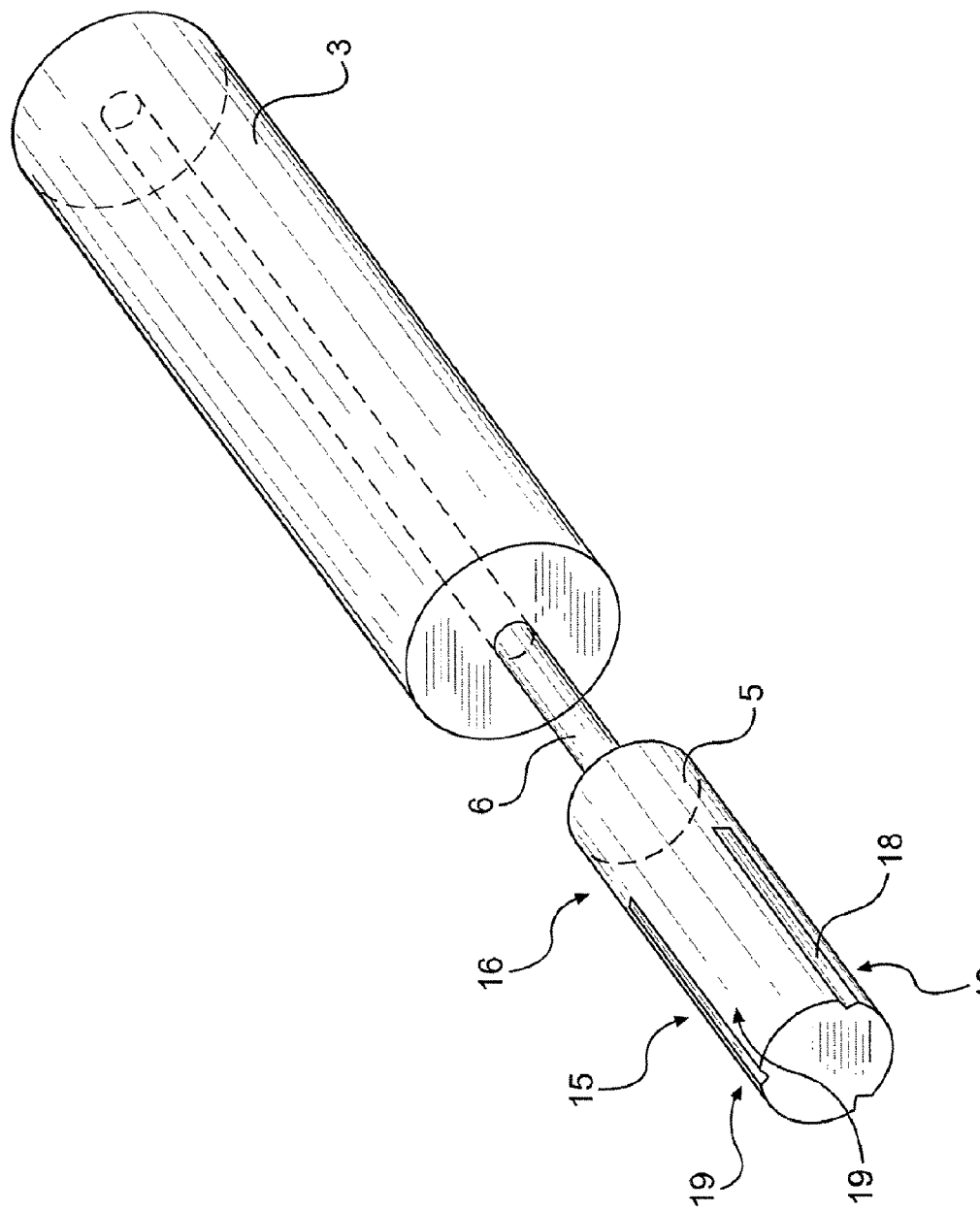
FIG. 2 is a perspective view of a lancet body, a lancet needle, and a sterile protector of the lancet system of FIG. 1.
Figure 3:
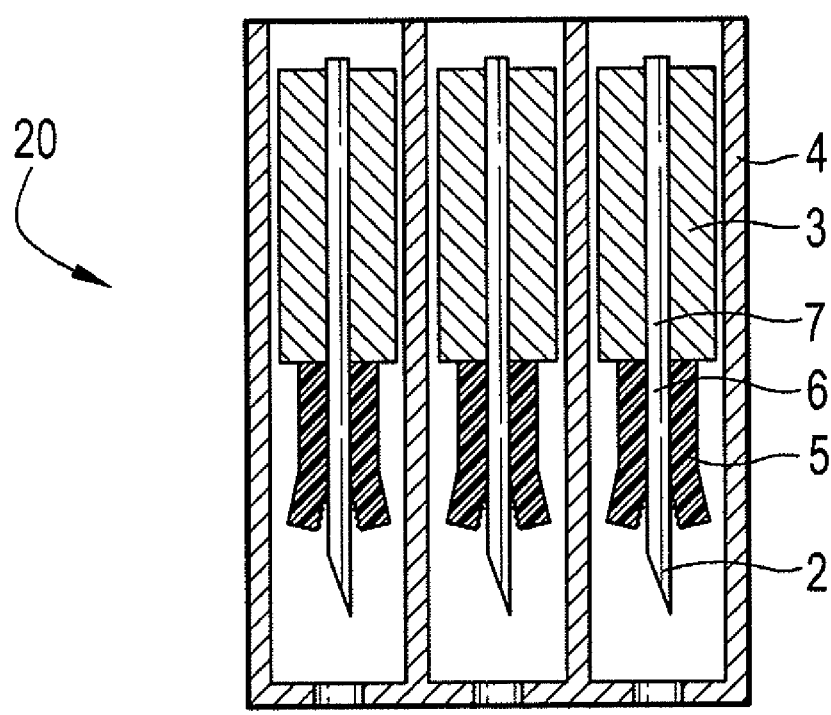
FIG. 3 is a schematic view in partial cross-section of a lancet magazine 20 having a plurality of lancets moveably mounted in chambers, each lancet having a tip and a sterile protector that surrounds the tip.

FIG. 2 shows the lancet body 3, the lancet needle 6, and the sterile protector 5 of the lancet system 1 from FIG. 1 prior to use (FIG. 1*a*). For the purposes of illustration, these elements of the lancet system 1 are illustrated without the hollow body or housing 4 surrounding them. The sterile protector 5 surrounds the lancet tip 2 (not shown) in a germproof manner. It has predetermined tear sections 18 which run substantially parallel to the lancet tip 2 and extend only along a portion (i.e., two-thirds) of the length of the sterile protector 5. The region 15 of the sterile protector 5 with the predetermined tear sections 18 is composed of a brittle material that has a tendency to undergo brittle fracture or separation rather than deformation, such as polyethylene filled with a high proportion of talc. The predetermined tear sections 18 divide the sterile protector 5 into subregions 19, which protrude from the lancet tip 2 after the sterile protector 5 is separated at the predetermined tear sections 18 (see FIG. 1*b*). The region 16 of the sterile protector 5 without predetermined tear sections does not break apart from the lancet tip during a puncturing operation. Instead, this region 16 continues to surround the lancet needle 6 such that the weakened portion or region 15 can be displaced away from the lancet tip 2 in the direction of the lancet body 3 (see FIG. 1*b*), but still remain attached to region 16 of the sterile protector 5 after separating.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

1 Lancet system
2 Lancet tip
3 Lancet body
4 Hollow body or housing
5 Sterile protector
6 Lancet needle
7 Needle body
8 First end of the hollow body or housing
9 First opening
10 Second end of the hollow body or housing
11 Second opening, outlet opening
12 Actuating means or Actuator
13 Puncture direction
14 Inner surface
15 Region of the sterile protector with predetermined tear sections
16 Region of the sterile protector without predetermined tear sections
17 Retraction direction
18 Predetermined tear sections
19 Subregions

What is claimed is:

1. A lancet system for withdrawing body fluid from a body part, comprising:
   a housing;
   a lancet having a tip; and
   a sterile protector that surrounds the tip, the sterile protector having a weakened portion that is brittle and is configured to undergo brittle fracture, the weakened portion of the sterile protector having a yield point of less than 50 N/mm2, the sterile protector at least partially separating along the weakened portion into sub-regions upon contact with the housing during a puncture movement, whereby the tip is released to perform a puncture.

2. The lancet system of claim 1, wherein the housing in which the lancet is reciprocably disposed has an opening through which the tip is exposed for puncture during a puncture movement of the lancet.

3. The lancet system of claim 2, wherein the tip extends from the opening during a puncture movement and retracts into the opening after the puncture movement.

4. The lancet system of claim 2, wherein the sterile protector at least partially separates when the sterile protector engages an inner surface of the housing.

5. The lancet system of claim 1, wherein the weakened portion comprises a thermoplastic, wax, or metal soap.

6. The lancet system of claim 5, wherein the weakened portion further comprises a filler selected from the group consisting of talc, graphite, and molybdenum disulfide.

7. The lancet system of claim 5, wherein the thermoplastic comprises polyethylene or polypropylene.

8. The lancet system of claim 1, wherein the weakened portion extends lengthwise along the sterile protector and is oriented substantially parallel to the tip.

9. The lancet system of claim 1, wherein the subregions protrude away from the tip after the sterile protector at least partially separates along the weakened portion.

10. The lancet system of claim 9, wherein the subregions remain connected to the sterile protector during the puncture movement.

11. The lancet system of claim 1, wherein the sterile protector comprises a substantially cylindrical cap.

12. The lancet system of claim 1, wherein the lancet defines a needle having the tip, the needle being at least partially surrounded by a lancet body.

13. The lancet system of claim 1, wherein the sterile protector is displaced away from the tip during the puncture movement.

14. The lancet system of claim 13, wherein the sterile protector slides along the lancet during the puncture movement.

15. The lancet system of claim 1, wherein the weakened portion comprises a plurality of weakened portions.

16. The lancet system of claim 1, wherein the weakened portion comprises a groove along which the sterile protector at least partially separates during a puncture movement.

17. A lancet system for pricking a body part and withdrawing body fluid, comprising:
    a magazine including a plurality of chambers; and
    a plurality of lancets, one of the plurality of lancets being movably mounted in a respective one of the plurality of chambers, each lancet comprising:
    a tip; and
    a sterile protector that surrounds the tip, the sterile protector having a weakened portion that is brittle and is configured to undergo brittle fracture, the weakened portion of the sterile protector having a yield point of less than 50 N/ram2, the sterile protector at least partially separating along the weakened portion into sub-regions upon contact with the chamber during a puncture movement, whereby the tip is released to perform a puncture.

18. The lancet system of claim 17, wherein each chamber includes a first opening configured for receiving a driving actuator.

19. The lancet system of claim 17, wherein, during a puncture movement, the sterile protector engages an inner surface of the chamber, thereby causing the sterile protector to at least partially separate at the weakened portion.

20. The lancet system of claim 17, wherein each chamber includes an outlet through which the tip extends during a puncture movement and through which the tip retracts into the chamber after the puncture movement.

21. The lancet system of claim 17, wherein the subregions protrude away from the tip after the sterile protector at least partially separates along the weakened portion.

22. The lancet system of claim 21, wherein the subregions remain connected to the sterile protector during the puncture movement.

23. The lancet system of claim 17, wherein the sterile protector is displaced away from the tip during the puncture movement.

24. The lancet system of claim 23, wherein the sterile protector slides along the lancet during the puncture movement.

25. A lancet system, comprising:
a housing having an opening;
a lancet disposed in the housing and having a tip configured to puncture a body part during a puncturing operation;
a sterile protector having a weakened portion that is brittle and is configured to undergo brittle fracture, the weakened portion of the sterile protector having a yield point of less than 50 N/mm2; and
the lancet being moveable between a first position and a second position, in the first position the tip being positioned within the housing and enclosed by the sterile protector, and in the second position the tip being exposed through the opening and the sterile protector being at least partially separated into sub-regions along the weakened portion upon contact with the housing.

26. The lancet system of claim 25, wherein the sterile protector comprises a substantially cylindrical cap.

27. The lancet system of claim 25, wherein the sterile protector comprises a first end section and a second end section, the second end section including the weakened portion.

28. The lancet system of claim 27, wherein, in the second position, the first end section circumscribes the lancet.

29. The lancet system of claim 27, wherein, in the second position, the second end section remains attached to the first end section.

30. The lancet system of claim 27, wherein, as the tip moves from the first position to the second position, the second end section engages an inner surface of the housing and at least partially separates along the weakened portion.

31. The lancet system of claim 30, wherein, as the second end section at least partially separates along the weakened portion, the second end section divides into the subregions, the subregions protruding away from the tip.

32. The lancet system of claim 30, wherein, after the second end section engages the inner surface of the housing, the sterile protector moves relative to the tip.

33. The lancet system of claim 32, wherein the sterile protector slides relative to the tip.

34. The lancet system of claim 25, wherein, in the second position, the subregions protrude away from the tip.

35. The lancet system of claim 1, wherein the sterile protector separates along an annular edge thereof.

36. The lancet system of claim 17, wherein the sterile protector separates along an annular edge thereof.

37. The lancet system of claim 25, wherein the sterile protector separates along an annular edge thereof.

38. The lancet system of claim 1, wherein the separation comprises a tear disposed along the lengthwise direction of the sterile protector.

39. The lancet system of claim 17, wherein the separation comprises a tear disposed along the lengthwise direction of the sterile protector.

40. The lancet system of claim 25, wherein the separation comprises a tear disposed along the lengthwise direction of the sterile protector.

* * * * *